(12) United States Patent
Flinchbaugh et al.

(10) Patent No.: US 12,419,732 B1
(45) Date of Patent: Sep. 23, 2025

(54) BLADDER MANAGEMENT DEVICE AND METHOD

(71) Applicants: David E. Flinchbaugh, Orlando, FL (US); Brian J. Awbrey, Lexington, MA (US); Allan F. Anderson, Flagler Beach, FL (US); Michael A. Rawers, Bonita Springs, FL (US); Paul Golis, Sanford, FL (US)

(72) Inventors: David E. Flinchbaugh, Orlando, FL (US); Brian J. Awbrey, Lexington, MA (US); Allan F. Anderson, Flagler Beach, FL (US); Michael A. Rawers, Bonita Springs, FL (US); Paul Golis, Sanford, FL (US)

( * ) Notice: Subject to any disclaimer, the term of this patent is extended or adjusted under 35 U.S.C. 154(b) by 0 days.

(21) Appl. No.: 18/812,921

(22) Filed: Aug. 22, 2024

(51) Int. Cl.
  *A61F 2/00* (2006.01)

(52) U.S. Cl.
  CPC ...... *A61F 2/0022* (2013.01); *A61F 2210/009* (2013.01); *A61F 2220/0016* (2013.01); *A61F 2250/0002* (2013.01)

(58) Field of Classification Search
  None
  See application file for complete search history.

(56) References Cited

U.S. PATENT DOCUMENTS

| | | |
|---|---|---|
| 4,865,588 A | 9/1989 | Flinchbaugh |
| 5,114,412 A | 5/1992 | Flinchbaugh |
| 5,971,972 A * | 10/1999 | Rosenbaum ......... A61M 5/162 604/411 |
| 6,307,517 B1 * | 10/2001 | Lee ..................... H01Q 1/2225 343/866 |
| D460,522 S | 7/2002 | Flinchbaugh |
| D478,662 S | 8/2003 | Flinchbaugh |
| 6,673,051 B2 | 1/2004 | Flinchbaugh |

(Continued)

FOREIGN PATENT DOCUMENTS

| | | |
|---|---|---|
| EP | 1645304 B1 | 4/2006 |
| WO | 1383557 B1 | 1/2004 |

OTHER PUBLICATIONS

Almasi, A. (May 24, 2018). Properly protect against overpressure. Setpoint Integrated Solutions. https://setpointis.com/properly-protect-against-overpressure/ (Year: 2018).*

(Continued)

*Primary Examiner* — Charles A Marmor, II
*Assistant Examiner* — Marc D. Honrath
(74) *Attorney, Agent, or Firm* — Camille A. Wilson; Wilson Dutra, PLLC (57) ABSTRACT

The present disclosure provides a bladder management device. The bladder management device may include a hard, durable body with an inflow portion and an outflow portion. In some implementations, the bladder management device may include a hollow body with a sample port and over-pressurization port and at least two magnets. In some aspects, the bladder management device may accept the influx of drainage fluid from a user. In some implementations, the bladder management device may include a shell protector and a microchip. A method may comprise the automatic and complete drainage of urinary fluid from a user via an AI bladder management diagnostic prosthetic sphincter device to fully and physiologically cycle the bladder.

9 Claims, 7 Drawing Sheets

(56) References Cited

U.S. PATENT DOCUMENTS

| | | | |
|---|---|---|---|
| 6,855,126 B2 | 2/2005 | Flinchbaugh | |
| 9,987,480 B2 | 6/2018 | McDaniel | |
| 10,058,481 B1* | 8/2018 | Russo | A61J 1/1406 |
| 2002/0139419 A1 | 10/2002 | Flinchbaugh | |
| 2002/0143318 A1* | 10/2002 | Flinchbaugh | A61M 5/16881 |
| | | | 604/179 |
| 2012/0286187 A1* | 11/2012 | Spolski | A61F 5/4405 |
| | | | 251/367 |
| 2012/0302938 A1* | 11/2012 | Browd | A61M 39/284 |
| | | | 604/9 |
| 2013/0331823 A1* | 12/2013 | Askem | A61M 1/96 |
| | | | 417/44.1 |
| 2014/0168917 A1* | 6/2014 | Marzano | H01G 4/40 |
| | | | 361/752 |
| 2014/0266624 A1* | 9/2014 | Van Bosch | G06K 7/10544 |
| | | | 235/492 |
| 2016/0137474 A1* | 5/2016 | Marantis | A61J 1/1406 |
| | | | 141/331 |
| 2016/0287858 A1* | 10/2016 | Truitt | A61M 39/105 |
| 2020/0339321 A1* | 10/2020 | Levy | B65D 51/002 |
| 2022/0101991 A1* | 3/2022 | Sowards | A61B 5/6852 |
| 2023/0248241 A1* | 8/2023 | Anttila | A61B 90/37 |
| | | | 600/411 |

OTHER PUBLICATIONS

Wikimedia Foundation. (Aug. 11, 2024). Radio-frequency identification. Wikipedia. https://en.wikipedia.org/w/index.php?title=Radio-frequency_identification&oldid=1239845869 (Year: 2024).*

* cited by examiner

Connect an inflow portion of a bladder management device to any patient indwelling urinary catheter and the outflow portion of the a bladder management device to a tubing connected to the drainage bag
710

Accept fluids from any urinary catheter through the inflow portion of the bladder management device and withdraw or analyze specimen fluids from the sample port at that upstream portion
720

Separate at least two self-sealing magnets located in a hollow chamber of the bladder management device
730

Receive the fluid that passes through an opening created by the separation of at least two self-sealing magnets, wherein the fluid is transferred to the drainage bag
740

Close the bladder management device, wherein the decrease of pressure caused by the complete influx of drainage of fluid from a user allows the re-attraction between at least two self-sealing magnets to draw them together
750

FIG. 7

BLADDER MANAGEMENT DEVICE AND METHOD

BACKGROUND

For thousands of years, humans have used catheters to gain access and subsequently drain urine from within the bladder to the outside of the body into a drainage bag. Catheters are routinely used to treat a wide variety of patient healthcare issues including bladder problems, sphincter and bladder nerve regulation problems, urinary retention problems, neurogenic bladder and as a temporary solution during, and after, difficult surgical procedures, trauma, ICU admissions or other serious illnesses.

While the catheter has incredible medical benefits, there are a gamut of dangerous side effects and serious risks of morbidity and mortality associated with their use: representing a major medical dilemma. Some of these risks include catheter biofilms, catheter blockage, catheter-associated urinary tract infections (CAUTIs), urethral trauma, bladder spasms, hematuria, and catheter leakage. Even the most advanced modern-day catheters are unable to avoid many of these issues, especially UTIs. CAUTIs occur due to incomplete bladder drainage and due to the loss of the physiologic advantage of bladder cycling: whereby bacteria seed and replicate within the urinary tract due to biofilms, catheter balloon urinary stagnation, encrustation of urine struvite crystals and the chronic catheter foreign body contamination effect. Despite the notorious risk of infection of 3-10% per day, compounding for each day of catheter use, medical professionals must employ the use of a urinary catheter on as many as 15% of all hospitalized patients.

These drawbacks to modern day indwelling urinary catheters introduce serious iatrogenic risk of CAUTI, antibiotic resistance and dangerous morbidity/mortality to patients who are often already dealing with serious medical conditions. A further major disadvantage and obstacle to modern day indwelling urinary catheter use is the billions of dollars of annual healthcare costs wasted to treat resultant CAUTI. If there was a catheter, or catheter adapter, that eliminated these drawbacks, removed the high incidence for UTIs and other catheter-induced issues, it would greatly elevate the level of catheter care, ease the burden of healthcare professionals and reduce the cost of care of these patients. Specifically, mimicking physiologic bladder cycling with an automatic external artificial sphincter prevents CAUTI and bacterial overgrowth of catheter biofilms.

Standardized modern efforts to decrease CAUTI are the SHEA/IDSA/APIC Practice Recommendations of Strategies to Prevent CAUTI in 2014 (updated in 2022): consisting primarily of restricting catheter use, to use non-catheter urinary management supplies (i.e. diapers), ensure that only trained HCP insert urinary catheters under aseptic conditions, routine use of antimicrobial/antiseptic coated catheters and catheter irrigation as a strategy to prevent infection. While heavily monitoring a patient and limiting access may achieve some results, a catheter adapter that appropriately self-regulates the urinary drainage of a patient with an artificial intelligence urinary bladder management diagnostic device and external prosthetic urinary sphincter solves this problem.

SUMMARY OF THE DISCLOSURE

What is needed is a bladder management device that improves the urinary fluid drainage process while reducing or eliminating unnecessary risk and complication by mimicking physiologic bladder cycling. A bladder management system that is self-sealing, wherein the fluid volume of an individual may increase or decrease the pressure placed on at least two magnets, wherein a certain threshold separates the at least one slidable or articulating or fully movable magnet from the at least one fixed magnet despite their magnetic attraction, which eliminates the majority of negative urine drainage side effects experienced by urinary catheter users. The described AI bladder management diagnostic prosthetic sphincter system is automatically cycling, perpetually operates without an external energy force and is fully self-energized by fluid dynamics.

In some embodiments, a bladder management device may include a hard, durable body with a hollow chamber. In some aspects, the bladder management device may include an inflow portion, wherein the inflow portion may be configured to accept the influx of drainage fluids from at least one user. In some aspects, the bladder management device may include an outflow portion comprised of distally oriented barbed fins, wherein the outflow portion may be configured to expel fluids to at least one external source. In some implementations, a sample port may be configured to enable the hollow chamber to collect a sterile fluid specimen. In some aspects, an over-pressurization port safety relief valve to ensure failsafe release of excess pressure in the hollow chamber. In some implementations, the bladder management device may include at least two magnets including at least one fixed magnet and one slidable or articulating or fully moveable magnet, wherein the at least one slidable or articulating or fully moveable magnet moves when a certain predetermined threshold of pressure may be experienced.

In some embodiments, the bladder management device may include a drainage bag and tubing, wherein at least one end of the tubing may connect to the outflow portion of the bladder management device and at least one end of the tubing may be connected to the drainage bag. In some aspects, the increase of pressure may be caused by an increase in fluid volume of at least one user may force at least one slidable or articulating or fully moveable magnet may move away from at least one fixed magnet to create a passageway for the fluid moving through the hollow chamber. In some implementations, the decrease in pressure caused by the influx of drainage fluid from the user may allow the attraction between the at least two magnets to move the at least one slidable or articulating or fully moveable magnet towards the at least one fixed magnet.

In some implementations, the sample port and the over-pressurization port are disc-like elastomeric diaphragms, wherein the diaphragm includes at least one circumferential biased tooth that includes a horizontal lower surface and an upwardly angled upper surface. In some aspects, the sample port and over-pressurization port may prevent the bladder management device from failure, wherein the sample port and over-pressurization port may release pressure if a predetermined threshold of pressure may be experienced. In some aspects, the sample port may be comprised an elastomeric-resealable or plastic material that may be pierceable by a syringe needle in a sterile fashion, wherein the sample port may be capable of resealing itself after the syringe needle may be withdrawn from the port. In some embodiments, the sample port and the over-pressurization port may be the same structural mechanism, wherein the structural mechanism may be configured to act as the sample port and the over-pressurization port.

In some embodiments, the bladder management device may include a shell protector configured to envelope the hard, durable body of the bladder management device, wherein the shell protector may provide electro-magnetic pulse protection to the bladder management device. In some aspects, the shell protector may be a sleeve that may be glued, press fit, elastically fit, or locked onto the outside surface of the bladder management device. In some implementations, the shell protector may be made from a predetermined combination of aluminum, carbon fiber, chromium, copper, or a nickel-iron soft ferromagnetic alloy.

In some embodiments, the shell protector may provide passive protection to the bladder management device, wherein the passive protection may include external electrical field interference such as from an MRI signal, laptop computer, static electricity, or a bedside cardiac monitor. In some aspects, the shell protector may provide active protection to the bladder management device, wherein the active protection may involve the shell protector emitting a predetermined threshold of radio frequencies to disrupt and interfere with signals that impact the functionality of the bladder management device. In some implementations, the bladder management device may include a microchip, wherein the microchip may be connected to the external surface of the bladder management device or the external surface of the shell protector.

In some aspects, the microchip may be configured to provide active pulse protection, wherein the active pulse protection eliminates risk of electromagnetic pulse malfunction. In some implementations, the microchip may be configured to send out radio frequency waves to prevent external interferences and to communicate with external electronic devices that may be configured to receive the radio frequency waves. In some embodiments, the microchip may include a power supply, wherein the microchip may be supplied energy by the power supply. In some aspects, the microchip may be coupled with the shell protector, wherein the microchip may be mounted onto the shell protector to reach the bladder management device. In some implementations, the microchip and the at least one external electronic devices may be coupled to communicate directly with the Electronic Health Record (EHR), external monitors, or include an artificial intelligence (AI) software.

A number of embodiments of the present disclosure will be described. While this specification contains many specific implementation details, these should not be construed as limitations on the scope of any disclosures or of what may be claimed, but rather as descriptions of features specific to particular embodiments of the present disclosure. It is understood to those skilled in the art that variations, modifications, and alterations may be apparent. It will be understood that various modifications may be made without departing from the spirit and scope of the disclosure.

BRIEF DESCRIPTION OF THE DRAWINGS

The accompanying drawings that are incorporated in and constitute a part of this specification illustrate several embodiments of the disclosure and, together with the description, serve to explain the principles of the disclosure.

The Figures are not necessarily drawn to scale, as their dimensions can be varied considerably without departing from the scope of the present disclosure.

DETAILED DESCRIPTION

The present disclosure provides generally for a bladder management device. In some aspects, the urine control flow device may be unidirectional, wherein a sample port may allow the sterile withdrawal of urine samples and an over-pressurization port as a fail-safe safety relief valve to ensure failsafe function. According to the present disclosure, a bladder management device may drain the influx of urine, wherein co-acting magnets may control the flow to automatically activate or deactivate the device to completely empty the bladder in a full cycle when, at least, partially filled with urine to prevent biofilm, CAUTI, loss of bladder muscle strength and bladder damage issues from occurring.

In the following sections, detailed descriptions of examples and methods of the disclosure will be given. The description of both preferred and alternative examples, though thorough, are exemplary only, and it is understood to those skilled in the art that variations, modifications, and alterations may be apparent. It is therefore to be understood that the examples do not limit the broadness of the aspects of the underlying disclosure as defined by the claims.

Glossary

Bladder management device: as used herein refers to a device configured to drain and then physiologically cycle the influx of urine from a catheter user and act as an automatic self-energizing external prosthetic urinary sphincter.

Catheter-Associated Urinary Tract Infection (CAUTI): as used herein refers to an iatrogenic urinary tract infection with a daily patient risk rate of 7-10%, which is associated with severe morbidity, significant mortality and wasteful excess healthcare costs.

Sample port and Over-Pressurization port: as used herein refers to a feature of the bladder management device that has the dual purpose of providing sterile access to the influx of urine fluid specimens and, also, for the purpose of expelling excess fluid pressure experienced as a safety relief valve to ensure failsafe function by the bladder management device.

Electronic Health Record (EHR): as used herein refers to a digital health record or health record software, which includes medical monitoring and reporting.

Distal oriented barbed fins: as used herein refers to protrusions located on the outflow portion of the bladder management device that are configured to secure the bladder management device to an external tubing.

Artificial Intelligence Software (AI): as used herein refers to software which is able to accumulate, self-analyze and report significant changes in the digital health record directly to the dashboard of medical care professionals in real-time based upon established parameters.

Shell Protector: as used herein refers to an accessory to the bladder management device that provides protection against electromagnetic interference and other types of electronic threats.

Inflow Portion: as used herein refers to the upstream section of the bladder management device where fluids are drained from a catheter user.

Outflow Portion: as used herein refers to the downstream section of the bladder management device with distally oriented fins where the bladder management device may connect to an external device to drain and deposit fluids received from the inflow portion.

Figure 1:
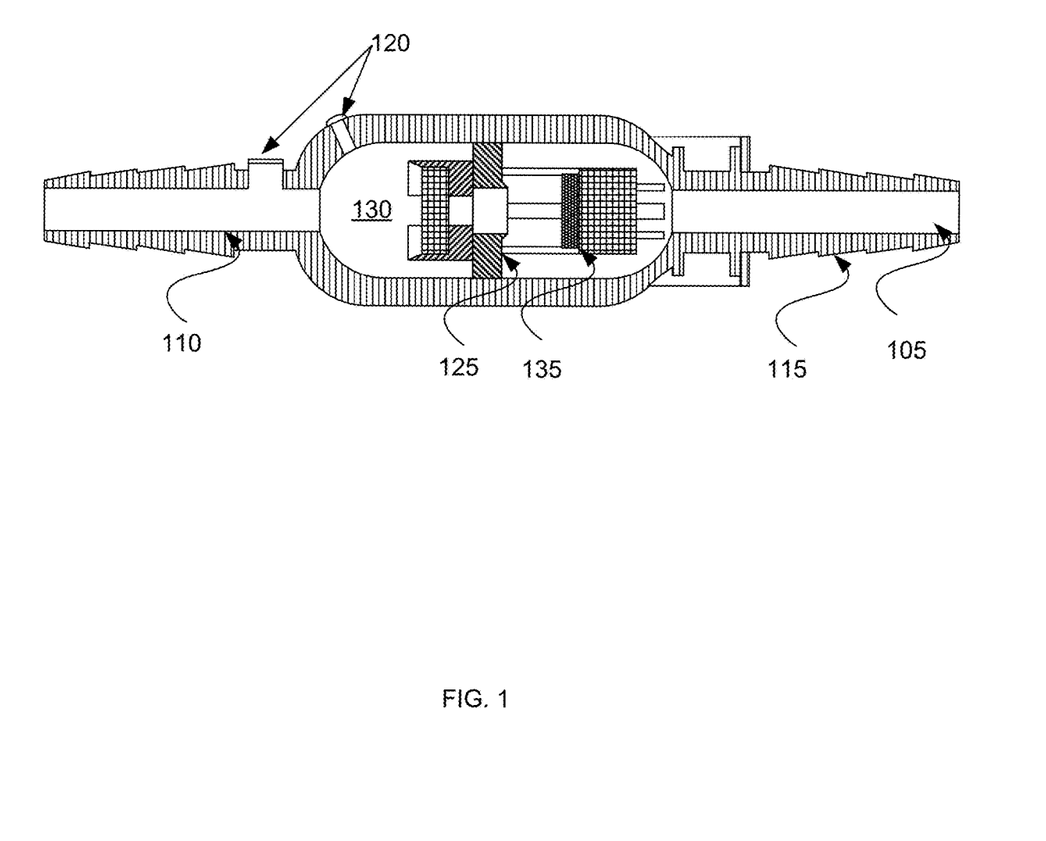
FIG. 1 illustrates a bladder management device, according to some embodiments of the present disclosure.

Referring now to FIG. 1, a bladder management device, according to some embodiments of the present disclosure, is illustrated. In some aspects, the bladder management device may include a hard, durable body with an inflow portion 105 and an outflow portion 110. In some aspects, the hard, durable body may be transparent. In some implementations, the hard, durable body may include a hollow chamber 130. In some embodiments, the hollow chamber 130 may include a combination sample port and over-pressurization port 120 and at least two magnets. In some embodiments, the sample port and over-pressurization port 120 may be located separately, wherein a sample port and an over-pressurization port are two different accessories to the bladder management device.

In some aspects, the bladder management device may be configured to accept the influx of drainage fluids from the inflow portion 105 through the hollow chamber 130 and send the drainage fluids out through the outflow portion 110. In some implementations, the drainage fluids may be drawn by the pressure induced by at least one external fluid source, wherein the pressure may induce the at least two magnets to move in such a way that allows the drainage fluid to move through the hollow chamber 130 from the inflow portion 105 to the outflow portion 110 of the device. In some aspects, the at least one external fluid source may be a user, wherein the user may be a patient. In some implementations, the user may be domestic or livestock animal or other type of living creature, as non-limiting examples.

In some embodiments, the outflow portion 110 may include a plurality of distally oriented barbed fins 115, wherein the plurality of distally oriented barbed fins 115 may be configured to connect the bladder management system to an external device. In some implementations, the sample port and over-pressurization port 120 may be upstream from at least two magnets that may be configured to sense the pressure of urine build up in a user's bladder, wherein the increase of pressure may separate the at least two magnets from one another to enable the urine to move through the bladder management device. In some aspects, the at least two magnets may include at least one fixed magnet 125 and one slidable or articulating or freely moving magnet 135, wherein the at least one fixed magnet 125 may be unmovable and the at least one slidable or articulating or fully movable magnet 135 may move when a certain predetermined threshold of pressure may be experienced.

In some aspects, the bladder management device may be self-sealing, wherein the increase or decrease of bladder fluid pressure in an individual may increase or decrease the pressure placed on the at least two magnets, wherein the certain pressure threshold separates the at least one slidable or articulating or freely moveable magnet 135 from the at least one fixed magnet 125 despite their magnetic attraction. In some implementations, the decrease in pressure may be outweighed by the force of attraction between the at least two magnets, wherein the at least two magnets may connect, thereby closing off a path through the bladder management device. In some aspects, the closed path of the bladder management device prevents the drainage of any fluids from the prosthetic sphincter despite further influx of user fluid.

Figure 2:
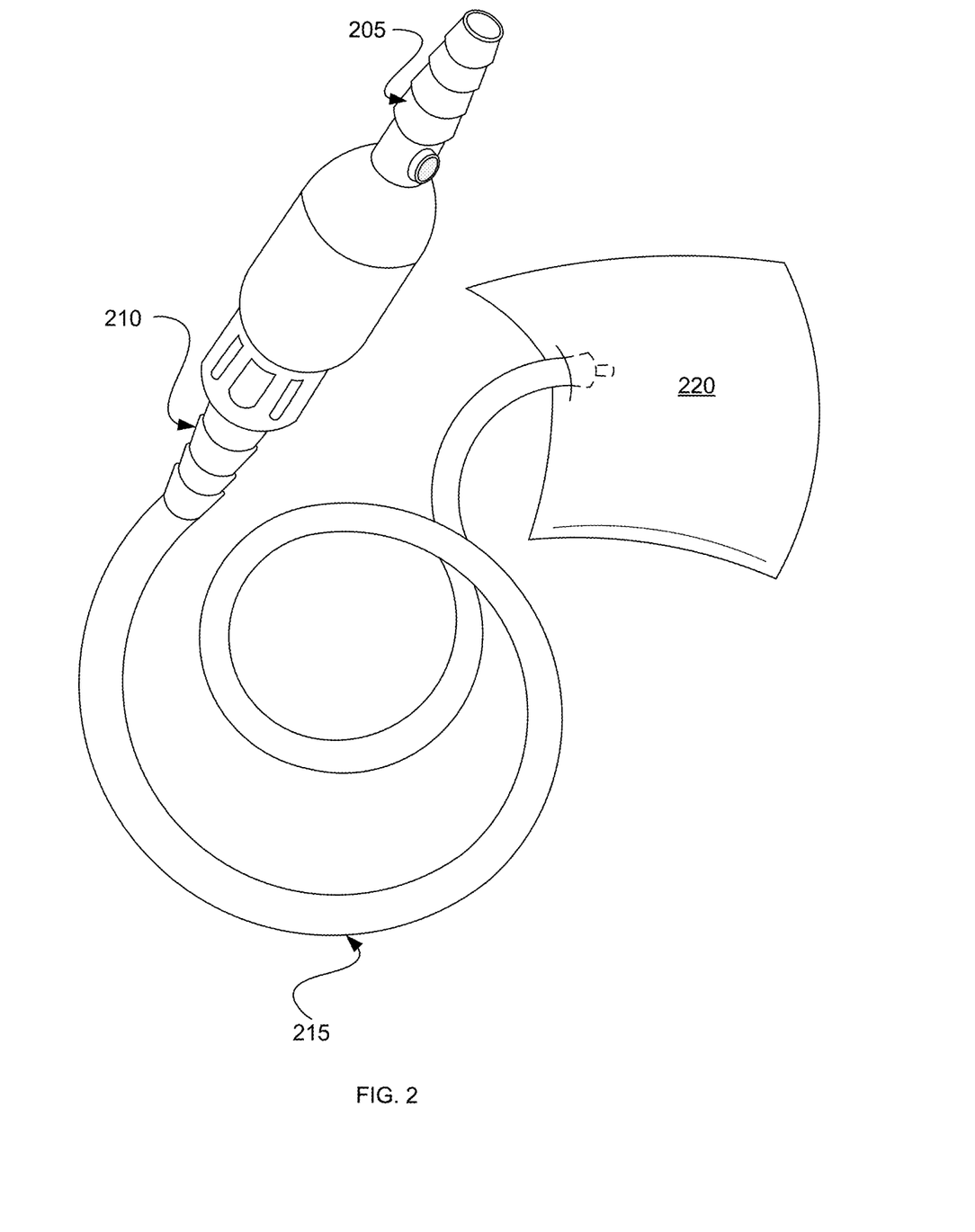
FIG. 2 illustrates a bladder management device with a drainage bag, according to some embodiments of the present disclosure.

Referring now to FIG. 2, a bladder management device with a drainage bag, according to some embodiments of the present disclosure, is illustrated. In some embodiments, the bladder management device may include an inflow portion 205 and an outflow portion 210. In some aspects, the outflow portion 210 may be connected to a tubing 215, wherein the tubing 215 may be attached to the drainage bag 220. By way of example and not limitation, fluids may travel from an individual, through the bladder management device and into the drainage bag 220, wherein the drainage bag 220 may be configured to store the drained urine.

In some implementations, the bladder management device may include at least two magnets. In some aspects, the increase of pressure may be configured to separate the at least two magnets to open the passageway of the bladder management device so that it may move into the drainage bag. In some embodiments, the outflow portion 210 may include a plurality of distally oriented barbed fins, wherein the plurality of distally oriented barbed fins may be placed inside the internal cavity of the tubing. In some aspects, placing the plurality of distally oriented barbed fins into the tubing may secure the bladder management device with the drainage bag 220.

Figure 3:
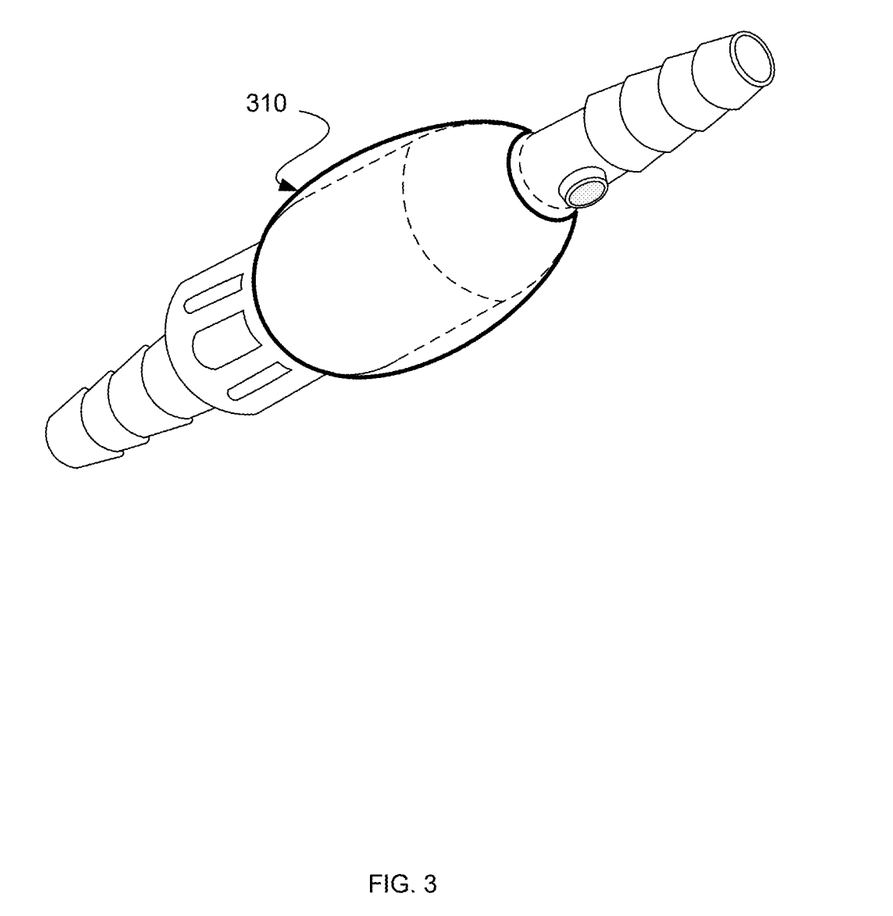
FIG. 3 illustrates a bladder management device with a shell protector, according to some embodiments of the present disclosure.

Referring now to FIG. 3, a bladder management device with a shell protector, according to some embodiments of the present disclosure, is illustrated. In some embodiments, the bladder management device may include a shell protector 310. In some aspects, the shell protector 310 may be configured to envelope the body of the bladder management device. In some implementations, the shell protector 310 may provide electro-magnetic pulse protection to prevent this bladder management device and critical medical devices from failing in the presence of foreign threat. In some aspects, the shell protector 310 may cover at least a portion of the bladder management device.

In some embodiments, the shell protector 310 may consist of materials that interfere with electromagnetic fields. By way of example and not limitation, the materials that make up the shell protector may include aluminum, carbon fiber, chromium, copper, or a nickel-iron soft ferromagnetic alloy. In some aspects, the shell protector 310 may be configured as a sleeve. In some implementations, the shell protector 310 may be attachable and removable, wherein the shell protector 310 may be placed over the bladder management device when the bladder management device may be in use. In some aspects, the shell protector 310 may be glued, press fit, elastically attached or locked onto the bladder management device, as a non-limiting example.

In some embodiments, the shell protector 310 may provide passive and active protection. In some aspects, the shell protectors' 310 passive protection may include radio frequency identification blocking or blocking shields that protect any enclosed electromagnetic components so that they are safe and unreadable from external electrical fields such as an MRI signal or bedside cardiac monitor, as a non-limiting example. In some implementations, the shell protector 310 may include active protection. In some aspects, the active shell protector 310 may be configured to emit a predetermined threshold of radio frequencies to disrupt and interfere with signals that may have an impact on the functionality of the bladder management device.

Figure 4:
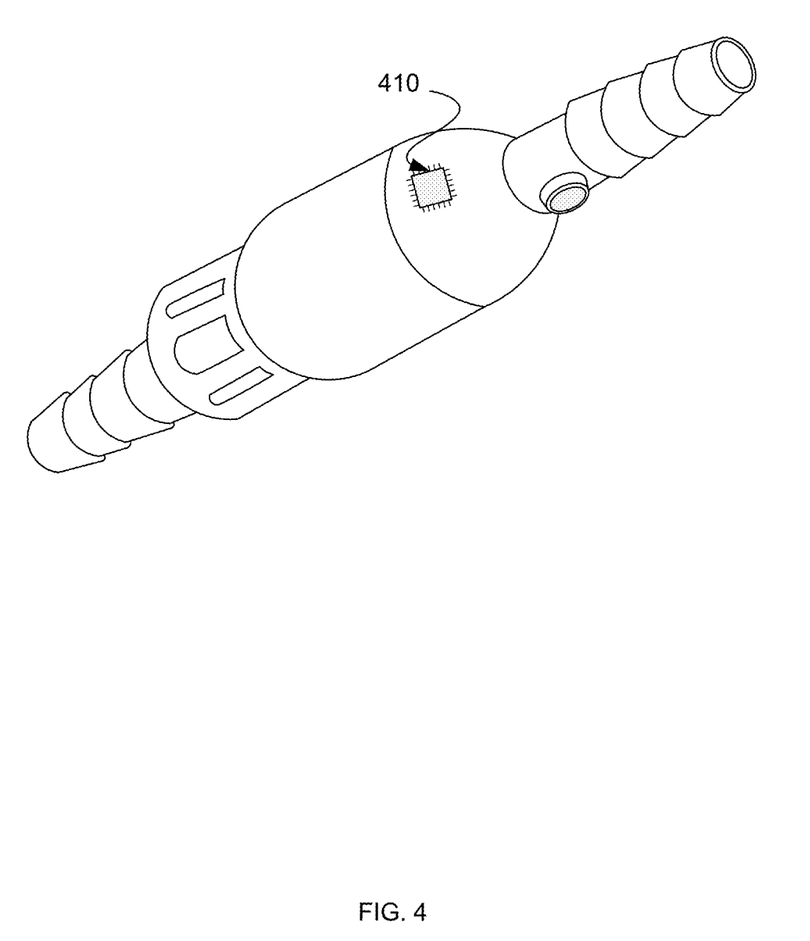
FIG. 4 illustrates a bladder management device with a microchip, according to some embodiments of the present disclosure.

Referring now to FIG. 4, a bladder management device with a microchip, according to some embodiments of the present disclosure, is illustrated. In some embodiments, the body of the bladder management device may include a microchip 410 on its external surface. In some aspects, the microchip 410 may be a small electronic device configured to perform a variety of electronic functions. In some implementations, the microchip 410 may be configured to provide active pulse protection or to send signals to an external device, as non-limiting examples.

In some implementations, the microchip 410 may provide active pulse protection for the bladder management device. In some aspects, active pulse protection may eliminate any risk of electromagnetic pulse malfunction to ensure the bladder management device is working properly. In some embodiments, the active pulse protection may be configured to send out radio frequency waves that may prevent unauthorized access to the bladder management device or any other effect from disrupting the device.

In some implementations, the microchip 410 may include a battery power source. In some aspects, the battery power source may be replaceable or rechargeable, as non-limiting examples. In some implementations, the replaceable battery source may include an accessible battery that may be attached and removed from the microchip 410. In some aspects, the rechargeable battery may include a rechargeable portion that may automatically recharge or may be charged through an external energy device or direct-wired to a low voltage power source.

In some embodiments, the microchip 410 may be communicatively coupled with at least one external device. In some aspects, the microchip 410 may be configured to send and receive signals from the at least one external device. By way of example and not limitation, the at least one external device may include a computer device, mobile device, or digital system. In some implementations, the at least one external device may be configured to analyze, process, and display the status and results of the bladder management device, wherein signals the microchip 410 receives from the bladder management device may be sent from the microchip 410 to the at least one external device.

In some implementations, the functioning of the bladder management device may be analyzed and controlled by the at least one external device. In some aspects, the at least one external device may activate the bladder management device to open or close upon command to drain fluids from a user. In some embodiments, the at least one external device may analyze the results of the upstream influx of drainage fluids within the upstream portion of the bladder management device, wherein details of the fluid and the bladder management device's user's health status may be, variously, digitally or visually or AI digitally revealed to bedside or physically-distant monitoring medical professionals, as well as permanently stored within the electronic medical record. As a non-limiting example, the upstream urine diagnostic analysis device and capabilities would be for point-of-service and instant digital measurement, EHR reporting and AI diagnostic analysis of: cell type and specificity, bacteria volume and identification, routine chemistry, color, pH, specific gravity, temperature, volume, real-time pressure metrics, cardiac enzymes, glucose, instant illicit drug detection, excreted medication toxic level detection and bladder metrics flow analysis.

In some embodiments, the microchip 410 and the at least one external device may be coupled to communicate, by any of several methods, directly with the Electronic Health Record (EHR), external monitors or include an artificial intelligence (AI) software. In some aspects, the AI software may be configured to receive and analyze signal from the bladder management device. In some implementations, the AI software may be configured to control the function of the bladder management device, wherein the AI software may prompt the bladder management device to drain, or fully stop the drainage of fluids from a user. In some embodiments, the AI software may be configured to determine the presence of any improving or untoward issues by instantly analyzing the urine of a user digitally and remotely. By way of example and not limitation, these issues may include catheter blockage, urinary tract infections (UTIs), urethral trauma, bladder spasms, hematuria, and catheter leakage.

Figure 5:
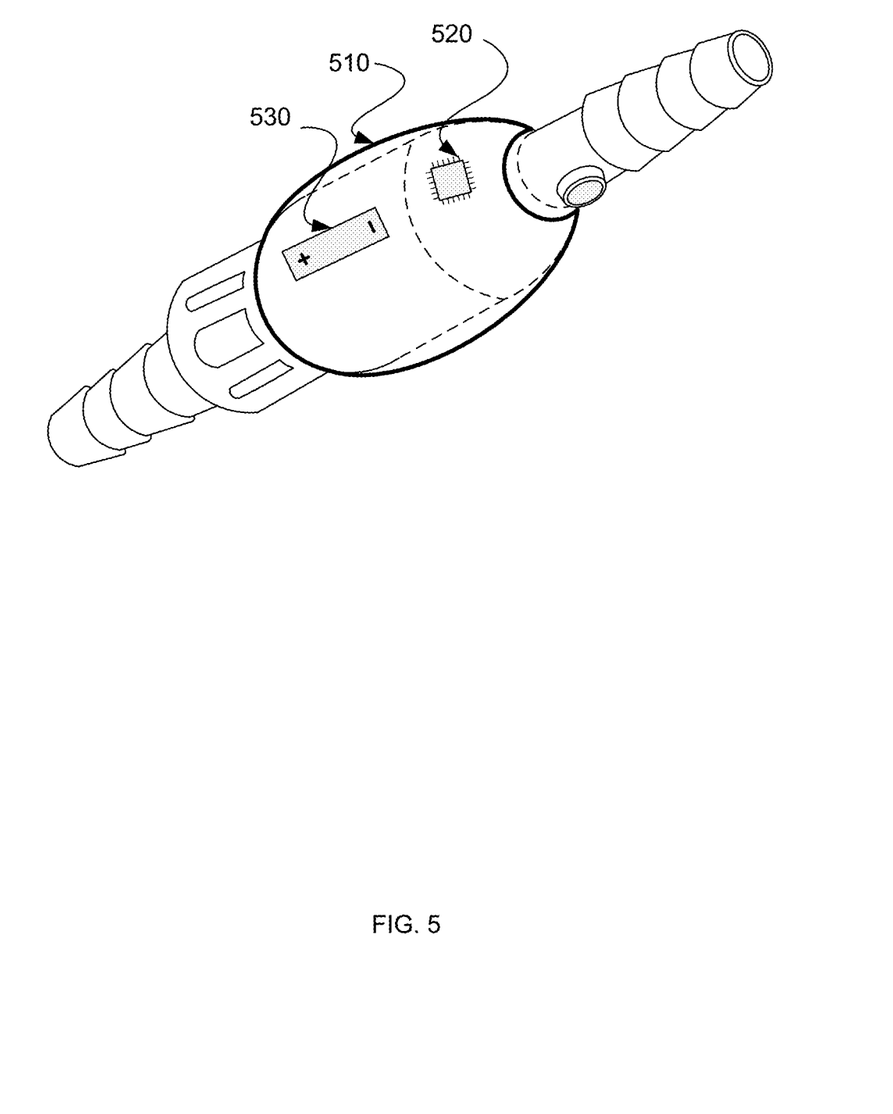
FIG. 5 illustrates a bladder management device with a microchip, according to some embodiments of the present disclosure.

Referring now to FIG. 5, a bladder management device with a microchip, according to some embodiments of the present disclosure, is illustrated. In some embodiments, the bladder management device may include a shell protector 510 and a microchip 520. In some aspects, the exterior surface of the shell protector 510 may include the microchip 520. In some implementations, the microchip 520 may be removable from the shell protector 510, wherein the microchip 520 may be replaced if necessary. In some aspects, the microchip 520 may access the bladder management device through the shell protector 510, wherein the microchip 520 may be configured to receive signals from the bladder management device to send the signals to an external device. In some embodiments, the microchip 520 may connect directly to the battery or any non-limiting local power source and/or at least one device to analyze details of the upstream fluid.

In some embodiments, the microchip 520 may include a battery source 530, wherein the battery source 530 may be replaceable or rechargeable, as non-limiting examples. In some aspects, the microchip 520 may include analytic sensors. In some implementations, the sensors may be configured to receive-detect neural signals actuating the magnets to open or close upon neural command, as a non-limiting example. In some aspects, the microchip 520 may communicate with the bladder management device, wherein the microchip 520 may send and receive signals to and from the bladder management device. In some aspects, the microchip 520 may communicate with at least one chemical analyzer, cell analyzer, fluid volume analyzer or urometric pressure gauge, as a non-limiting example.

By way of example and not limitation, the coupled microchips 520 of the bladder management device may communicate with one another to optimize, or customize, the fluid drainage process. In some implementations, the shell protector 510 may protect the microchip 520 from digital interference and electromagnetic pulses, as non-limiting examples. In some embodiments, the shell protector 510 may be digitally coupled to the microchip 520, wherein the microchip 520 may receive and send signals from the bladder management device and shell protector 510. In some implementations, the microchip 520 may be communicatively coupled with at least one external device, wherein the at least one external device may be configured to send and receive signals from the microchip 520.

In some aspects, the at least one external device may include a computer device or mobile device, as non-limiting examples. In some embodiments, the at least one external device may be configured to analyze, process, and display the information received by the signals of the microchip 520.

In some aspects, the at least one external device may display the information on a digital display. In some embodiments, the at least one external device may be configured to control the shell protector 510 and the bladder management device, wherein the microchip 520 may receive signals from the at least one external device and send directions to the shell protector 510 and the bladder management device.

Figure 6:
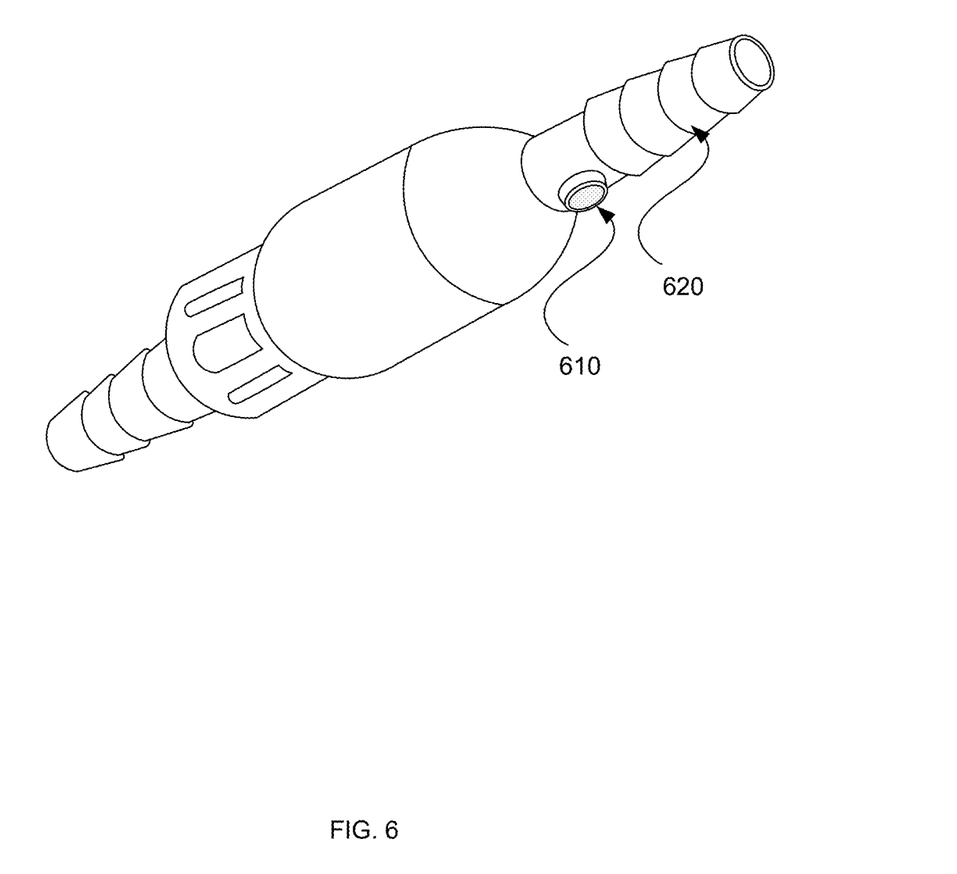
FIG. 6 illustrates a bladder management device with a sample port and an over-pressurization port, according to some embodiments of the present disclosure.

Referring now to FIG. 6, a bladder management device with a sample port and over-pressurization port fail-safe relief valve, according to some embodiments of the present disclosure, is illustrated. In some embodiments, the sample port and over-pressurization port 610 may prevent the bladder management device from failure. In some implementations, the sample port and over-pressurization port 610 may be located on the bladder management device at the inflow portion 620, wherein the sample port and over-pressurization port 610 is located before the distally oriented barbed fins. In some aspects, the sample port and over-pressurization port 610 may be externally or internally mounted on the bladder management device. In some embodiments, the sample port and over-pressurization port 610 fail-safe relief valve may be a disc-like elastomeric diaphragm, wherein the diaphragm may include at least one circumferential biased tooth. In some aspects, the circumferential biased tooth may include a horizontal lower surface and an upwardly angled upper surface.

In some implementations, the sample port and over-pressurization port 610 may serve as an over-pressurization port, wherein the over-pressurization port may be used as a pressure relief fail-safe valve, wherein when a predetermined threshold of pressure may be experienced, the valve may open to release the pressure. By way of example and not limitation, the predetermined threshold of pressure may be any supraphysiologic bladder pressure greater than 40 cm of fluids. In some aspects, the over-pressurization port may prevent excess pressurization of the upstream fluid path, wherein the over pressurization of the fluid path may be caused by pathway obstruction, magnet failure, patient positional obstruction, intentional obstruction, bacterial obstruction, or debris buildup, as non-limiting examples.

In some embodiments, the sample port and over-pressurization port 610 may be used to sample a sterile urine specimen under direct visualization in the device. In some aspects, the sample port and over-pressurization port 610 may allow the bladder management device to collect sterile fluid specimen without breach of the sterile enclosed system. In some embodiments, the sample port and over-pressurization port 610 may enable the device to catch the freshest fluids as required by medical-grade regulations. In some implementations, the sample port and over-pressurization port 610 may be comprised of a disc-like elastomeric or plastic material that may be pierceable by a conventional, sterile syringe needle, wherein the sample port and over-pressurization port 610 may be capable of sterilely and fully resealing itself after the needle may be withdrawn.

Figure 7:
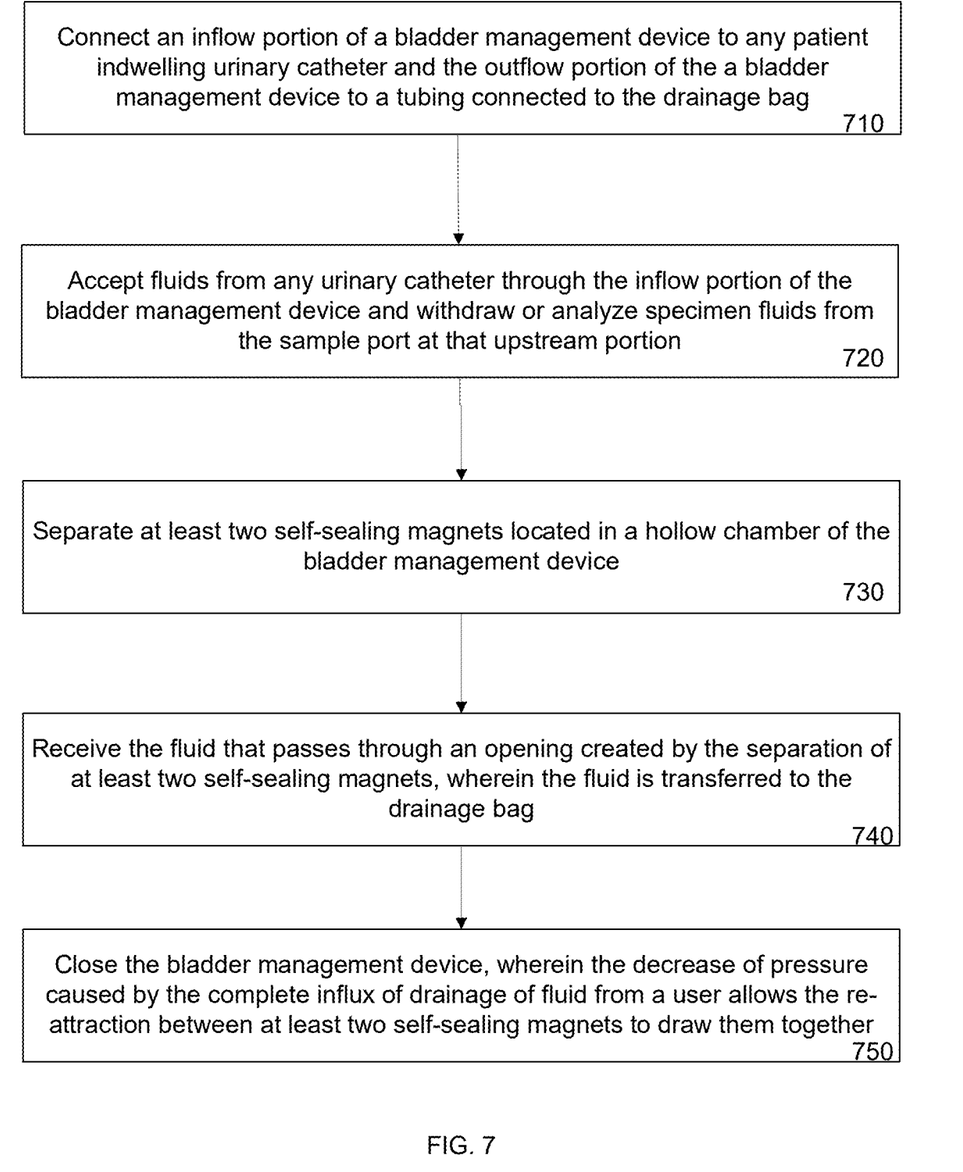
FIG. 7 is a flow chart illustrating the sequential functions of a self-sealing and automatically and perpetually self-energized bladder management prosthetic urinary sphincter device.

Referring now to FIG. 7, a method for a bladder management system, according to some embodiments of the present disclosure, is illustrated. At 710, the method includes connecting an inflow portion of a bladder management device to any patient indwelling urinary catheter and the outflow portion of a bladder management device to a tubing connected to a drainage bag. In some aspects, at 720 may further include the influx of drainage fluids from a user through the inflow portion of the bladder management device and withdrawing or analyzing specimen fluids from the sample port at that upstream portion. At 730, the method may include separating at least two self-sealing magnets located in a hollow chamber of the bladder management device, wherein the increase in certain and safe fluid pressure within the bladder of the user forces an at least one slidable or articulating or fully movable magnet to move away from the at least one fixed magnet.

At 740, the method may involve receiving the fluid that passes through an opening created by the separation of at least two self-sealing magnets, wherein the fluid passes through an outflow portion of the bladder management device and into a drainage tubing that connects to the drainage bag. At 750, the method may further include closing the bladder management device, wherein the decrease of pressure caused by the complete influx of drainage fluid from the user allows the re-attraction between the at least two magnets to move the at least one slidable or articulating or fully movable magnet moves towards the at least one fixed magnet. In some aspects, the closing of the bladder management device may indicate that a user's fluids have been completely and successfully drained, emptying the bladder of all fluid. This would herald the completion of the bladder emptying cycle to automatically start again, fully self-powered by fluid dynamic forces.

CONCLUSION

A number of embodiments of the present disclosure have been described. While this specification contains many specific implementation details, these should not be construed as limitations on the scope of any disclosures or of what may be claimed, but rather as descriptions of features specific to particular embodiments of the present disclosure.

Certain features that are described in this specification in the context of separate embodiments can also be implemented in combination or in a single embodiment. Conversely, various features that are described in the context of a single embodiment can also be implemented in combination in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous.

Moreover, the separation of various system components in the embodiments described above should not be understood as requiring such separation in all embodiments, and it should be understood that the described components and systems can generally be integrated together in a single product or packaged into multiple products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order show, or sequential order, to achieve desirable results. In certain implementations, multitasking and parallel processing may be advantageous. Nevertheless, it will be understood that various modifications may be made without departing from the spirit and scope of the claimed disclosure.

Reference in this specification to "one embodiment," "an embodiment," any other phrase mentioning the word "embodiment", "aspect", or "implementation" means that a particular feature, structure, or characteristic described in connection with the embodiment is included in at least one embodiment of the disclosure and also means that any particular feature, structure, or characteristic described in connection with one embodiment can be included in any embodiment or can be omitted or excluded from any embodiment. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others and may be omitted from any embodiment. Furthermore, any particular feature, structure, or characteristic described herein may be optional.

Similarly, various requirements are described which may be requirements for some embodiments, but not other embodiments. Where appropriate any of the features discussed herein in relation to one aspect or embodiment of the invention may be applied to another aspect or embodiment of the invention. Similarly, where appropriate any of the features discussed herein in relation to one aspect or embodiment of the invention may be optional with respect to and/or omitted from that aspect or embodiment of the invention or any other aspect or embodiment of the invention discussed or disclosed herein.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted.

It will be appreciated that the same thing can be said in more than one way. Consequently, alternative language and synonyms may be used for any one or more of the terms discussed herein. No special significance is to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," "aft," "forward," "inboard," "outboard," "upstream," "downstream," "indwelling," "EHR", and "below" used herein are merely for ease of description and refer to the orientation of the components as shown in the figures. It should be understood that any orientation of the components described herein is within the scope of the present invention.

What is claimed is:

1. A bladder management device comprising:
   a hard, durable body with a hollow chamber including:
   an inflow portion, wherein the inflow portion is configured to accept an influx of drainage fluids from at least one user;
   an outflow portion comprised of distally oriented barbed fins, wherein the outflow portion is configured to expel fluids to at least one external source;
   a sample port to enable collection of a sterile fluid specimen in the hollow chamber;
   an over-pressurization port configured as a fail-safe to release excess fluid pressure in the hollow chamber;
   at least two magnets including at least one fixed magnet and at least one slidable magnet, wherein the at least one slidable magnet moves when a predetermined threshold of pressure is experienced;
   a shell protector configured to envelope the hard, durable body, wherein the shell protector provides electromagnetic pulse protection to the bladder management device; and
   a microchip externally mounted to the shell protector, wherein the microchip includes a power supply, and wherein the microchip is configured to provide electromagnetic pulse protection to the bladder management device by emitting a predetermined threshold of radio frequencies to disrupt and interfere with signals that impact a functionality of the bladder management device.

2. The bladder management device of claim 1, wherein the shell protector is a sleeve that is glued, press fit, elastically fit, or locked onto an outside surface of the bladder management device.

3. The bladder management device of claim 1, wherein the shell protector is made from a predetermined combination of aluminum, carbon fiber, chromium, copper, or a nickel-iron soft ferromagnetic alloy.

4. The bladder management device of claim 1, wherein the shell protector provides passive protection to the bladder management device, wherein the passive protection includes external electrical field interference.

5. The bladder management device of claim 1, wherein the microchip is configured to provide active pulse protection, wherein the active pulse protection eliminates risk of electromagnetic pulse malfunction.

6. The bladder management device of claim 1, wherein the microchip is configured to send out radio frequency waves to prevent external interference and to communicate with external electronic devices that are configured to receive the radio frequency waves.

7. The bladder management device of claim 1, wherein the microchip is supplied energy by the power supply.

8. The bladder management device of claim 1, wherein the microchip is mounted onto the shell protector to reach the bladder management device, wherein the shell protector includes an opening to receive a portion of the microchip configured to allow the microchip access to the bladder management device.

9. The bladder management device of claim 1, wherein the microchip and at least one external electronic device may be coupled to communicate directly with an Electronic Health Record (EHR), external monitors, or include an artificial intelligence (AI) software.

\* \* \* \* \*